United States Patent [19]

Masunaga et al.

[11] Patent Number: 5,714,461
[45] Date of Patent: Feb. 3, 1998

[54] MEDICINAL COMPOSITIONS FOR THE IMPROVEMENT OF BLOOD COAGULATION COMPRISING TCF-II

[75] Inventors: Hiroaki Masunaga; Nobuaki Fujise, both of Shimotsuga-gun, Japan

[73] Assignee: Snow Brand Milk Products Co., Ltd., Japan

[21] Appl. No.: 367,247

[22] PCT Filed: Jul. 14, 1993

[86] PCT No.: PCT/JP93/00974

§ 371 Date: Jan. 11, 1995

§ 102(e) Date: Jan. 11, 1995

[87] PCT Pub. No.: WO94/02165

PCT Pub. Date: Feb. 3, 1994

[30] Foreign Application Priority Data

Jul. 16, 1992 [JP] Japan ................................. 4-212228
Apr. 21, 1993 [JP] Japan ................................. 5-117809

[51] Int. Cl.$^6$ ............................ A61K 38/16; C07K 1/00; C12P 21/06
[52] U.S. Cl. ............................... 514/8; 514/12; 514/21; 530/350; 530/380; 530/397; 530/399; 435/69.1; 435/69.4
[58] Field of Search ........................ 514/8, 12, 21; 530/350, 380, 397, 399; 435/69.1, 69.4

[56] References Cited

U.S. PATENT DOCUMENTS

| 4,076,701 | 2/1978 | Burton et al. | 260/112 B |
|---|---|---|---|
| 4,490,549 | 12/1984 | Johnson | 549/396 |
| 5,091,511 | 2/1992 | Sone et al. | 530/351 |
| 5,328,836 | 7/1994 | Shima et al. | 435/69.4 |
| 5,510,327 | 4/1996 | Hayasaka et al. | 514/8 |

FOREIGN PATENT DOCUMENTS

| 2116192 | 8/1994 | Canada . |
|---|---|---|
| 0519728A2 | 12/1992 | European Pat. Off. . |
| 0588477A2 | 3/1994 | European Pat. Off. . |
| 0462277B1 | 6/1995 | European Pat. Off. . |
| WO90/10651 | 9/1990 | WIPO . |
| WO 94/14845 | 7/1994 | WIPO . |

OTHER PUBLICATIONS

S. Sone, "Kinetics and Function of Tumor Cytotoxic Factor(s) Produced by Human Blood Monocytes Activated to the Tumoricidal State" *JNCI* 74(3):583–590 (1985).

S. Sone, "Potentiation of Direct Antitumor Cytotoxicity and Production of Tumor Cytolytic Factors in Human Blood Monocytes by Human Recombinant Interferon–Gamma and Muramyl Dipeptide Derivatives" *Cancer Immunol. Immunother.* 21:93–99 (1986).

S. Sone, "Effector Mechanism of Human Monocyte–Mediated Cytotoxicity: Role of a New Tumor Cytotoxic Factor Distinct from Interleukin 1 and Tumor Necrosis Factor α" *Biotherapy* 1:233–243 (1989).

*Primary Examiner*—Cecilia J. Tsang
*Assistant Examiner*—Abdel A. Mohamed
*Attorney, Agent, or Firm*—Testa, Hurwitz & Thibeault, LLP

[57] ABSTRACT

Blood coagulation normalizing agents comprising effective ingredient of TCF-II.

The blood coagulation normalizing agents of the present invention comprised of glycoprotein TCF-II produced by human fibroblast cells and accelerates the production of blood coagulation factor and increases platelet count to treat abnormal blood coagulation such as disseminated intravascular coagulation (DIC) and decreased platelet count caused by administration of cisplatin.

11 Claims, 6 Drawing Sheets

MEDICINAL COMPOSITIONS FOR THE IMPROVEMENT OF BLOOD COAGULATION COMPRISING TCF-II

FIELD OF THE INVENTION

This invention relates to medicinal compositions for the normalization of blood coagulation or treatment of abnormal blood coagulation, comprising a glycoprotein produced by human fibroblast cells, TCF-II (tumor cytotoxic factor-II), more particularly agents for the treatment of disseminated intravascular coagulation (DIC) syndrome, increase of platelet count and prevention of thrombocytopenia.

DESCRIPTION OF THE PRIOR ART

Biologically active substances produced by human derived fibroblast cells, for example, β-interferon as a tumor cytotoxic factor, have been well known. Biologically active substances produced by fibroblast cells other than β-interferon such as a tumor cytotoxic glycoprotein called CBF is disclosed in Japanese Patent Laid-open Publication No. 146293 (1983). A tumor growth inhibitory factor (INF) with molecular weight of 35,000–48,000, which is purified from culture broth of fibroblasts derived from human tissue, is disclosed in Japanese Patent Laid-open Publication No. 33120 (1986). Furthermore, a tumor necrosis factor-like substance which is purified from the culture broth of fibroblasts, a fibroblast-derived necrosis factor, FNF, and a physiologically active substance with cytotoxic activity, which is produced by animal-derived fibroblasts and has a molecular weight of 40,000 to 60,000 and an isoelectric point of pH 5.0±0.5, are disclosed in Japanese Patent Laid-open Publication No. 1872 (1986) and Japanese Patent Laid-open No. 103021 (1987), respectively. In addition, all the primary amino acid sequence and cDNA encoding the amino acid sequence of a tumor cytotoxic factor, which is obtained from the culture broth of human-derived fibroblasts, with a molecular weight of 36,000±1,000 and an isoelectric point of pH 10.5 or higher are disclosed in Japanese Patent Laid-open No. 10988 (1989). The inventors have been investigating antitumor substances derived from human fibroblast cells and found a new antitumor protein, which is different from antitumor proteins hitherto reported. Furthermore, the inventors successfully cloned a cDNA encoding the protein, determined its all the primary amino acid sequence, and confirmed usefulness of the protein. The new antitumor protein and its gene were disclosed in the inventors' International Patent Publication No. 10651 (1990). The new antitumor protein was called as TCF-II.

TCF-II has both potent antitumor activity and proliferation stimulative activity for normal cells and is a member of the HGF (hepatocyte growth factor) group. Molecular weight determination of TCF-II with SDS electrophoresis showed a common band, A chain, with 78,000±2,000 and two bands, B and C chains, with 30,000±2,000 and 26,000±2,000, respectively.

TCF-II may be used for the regeneration of liver after the hepatectomy due to its proliferation stimulative effect on hepatocytes. However, no effect of TCF-II on diseases related to abnormal blood coagulation such as DIC and thrombocytopenia has been known.

DIC accompanies with various basal diseases and frequently causes blood clotting in systemic fine blood vessels. It impairs functions of many organs and tends to result in marked hemorrhages due to consumption coagulopathy and hyperfibrinolysis. The basal diseases causing DIC include malignant tumor, leukemia, sepsis, infectious diseases, obstetric diseases such as placental abruption and amniotic fluid embolism, and shock in a descending order. Diseases frequently accompanied with DIC include leukemia, malignant lymphoma, myeloma, collagen disease, and liver diseases in. descending order. In addition to risk factors such as surgical invasion, administration of an antitumor agent, infectious diseases and shock may accelerate the onset of DIC. During the onset of DIC, coagulation factors such as blood coagulation factors I, II, V, VIII and XIII are consumed and their blood level decrease. Platelets are consumed in thrombus of systemic fine blood vessels by adhesion and coagulation in damaged subcutaneous tissues and incorporation in fibrin. Fibrinolytic system is activated by influx of tissue activator into blood stream, formation of kallikrein and so forth after the activation of coagulation system and the fibrin degradation products (FDP) are formed by secondary fibrinolysis. Decrease of plasma fibrinogen, elongation of prothrombin time and decrease of platelet count can markedly be observed. Widely spread tendency of hemorrhage has been known to be due to massive consumption of antithrombin III or $\alpha_2$-antiplasmin caused by inactivation of thrombin and plasmin. Furthermore, DIC is known to exhibit symptoms of disturbed production of vitamin K dependent coagulation factor due to liver damage, intoxication and other causes, abnormal protein metabolism including cachexia and adverse effects of medicines, bleeding and insufficient hemostasis due to thrombocytopenia.

Heretofore, no effective treatment of DIC has been found and according to symptoms of DIC, only palliative therapy such as administration of warfarin and fibrinogen to hemorrhagic tendency have been performed. In addition, thrombocytopenia also occurs by the administration of medicines including antitumor agents and by various diseases, but no preventive treatment to the decrease of platelets has been found.

DISCLOSURE OF THE INVENTION

The inventors noticed the biological activity of TCF-II and have been investigating the use of TCF-II as an antitumor agent and a diagnostic marker of the diseases.

The inventors found in the investigation on actions of TCF-II for liver that TCF-II provides not only proliferation of hepatocytes but also therapeutic effects on various abnormal blood coagulation accompanied by DIC. Furthermore, the inventors found that TCF-II dose dependently increases platelet count and inhibits the decrease of platelet count due to administration of antitumor agents. Heretofore, the therapeutic effect of TCF-II on various blood coagulation disorder such as disseminated intravascular coagulation (DIC) or prevention against decrease of platelet count has not been confirmed. The increase of platelet count and therapeutic effect of TCF-II on abnormal blood coagulation and thrombocytopenia are surprising.

An object of the invention is to provide a treatment agent comprising TCF-II as an effective ingredient against abnormal blood coagulation.

The agents containing TCF-II as an effective ingredient to normalize blood coagulation practically include blood coagulation normalizing agent, platelet increasing agent and thrombocytopenia preventive agent.

The effective ingredient of the present invention is a known glycoprotein (TCF-II) derived from human fibroblast cells as described previously.

On SDS-polyacrylamide gel electrophoresis, TCF-II showed bands with M.W. 78,000±2,000 and 74,000±2,000 under nonreduced conditions, and also showed a common band A with M.W. 52,000±2,000 in the reduced condition and band B with M.W. 30,000±2,000 and band C with M.W. 26,000±2,000 under reduced conditions. TCF-II also showed an isoelectric point of pH 7.4–8.6 and was determined as a glycoprotein having the primary amino acid sequence composed of 723 amino acids.

The above mentioned TCF-II can be obtained by concentration of a human fibroblast cell culture broth, adsorption and solution by ion exchange chromatography of the concentrate and affinity chromatography of the eluate (WO90/10651) or by a genetic engineering method (WO92/01053).

TCF-II obtained from human fibroblast cells cultured by the method disclosed in WO90/10651 can be used. Furthermore, TCF-II produced by a gene engineering technique using microorganisms or other cells transfected with the gene having oligonucleotide sequence disclosed in the above mentioned patent publication may be used. The production of TCF-II by the genetic engineering method may be carried out by the method invented by the present inventors and disclosed in WO92/01053. In addition, TCF-II analogues having different sugar chains or no sugar moieties produced by different host cells or microorganisms may also be used. However, presence of sugar moieties is preferable because of their participation in the in vivo metabolic rate.

TCF-II can be concentrated and purified by conventional isolation and purification methods, for example, precipitation with an organic solvent, salting-out, gel filtration chromatography, affinity chromatography using a monoclonal antibody and electrophoresis. The purification by affinity chromatography using a monoclonal antibody disclosed in Japanese Patent-Application No. 177236 (1991) by the present inventors may be applied.

The resultant purified TCF-II may be kept under lyophilization or deep freezing.

Furthermore, the blood coagulation normalizing agent of the present invention may be administered as injection preparations intravenous, and any route such as intraarterial, intramuscular and subcutaneous injections can be selected. Blood coagulants such as fibrinogen, coagulation controlling factors such as antithrombin III and drugs such as FOY, a protease inhibitor used for the treatment of DIC are also used concomitantly.

The injection preparations of TCF-II may be used alone or in combination with above mentioned medicines and adjuvants such as human serum albumin, surface active agents, amino acids and sugars.

The doses of TCF-II included in the blood coagulation normalizing agents of the present invention can be determined according to the symptoms and conditions and the age of the patients and generally administered in a dose range of 100–30,000 µg TCF-II/kg, preferably, 500–3,000 µg TCF-II/kg, 1–7 times a week. Long term administration may be used according to the symptoms and conditions of the patients.

Following diseases may be illustrated as indications of the present invention.

(1) Various diseases accompanying decrease of platelet, particularly decreased production of platelet due to radiation damage and medicines such as antitumor agents, aplastic anemia and related diseases, substitution of hematopoietic tissue due to myelophthisis, leukemia, malignant lymphoma, myelofibrosis and metastasis of tumors to bone, megalocytic anemia due to deficiency of vitamin $B_{12}$ and folic acid, production of ineffective platelet due to paroxysmal nocturnal hemoglobinuria, congenital low production of platelet and thrombopoietin deficient infections such as sepsis and AIDS.

(2) Various diseases accompanied with accelerated platelet destruction, particularly DIC, disturbance of fine blood vessels, massive blood transfusion, hyperglyceridemia, drug induced destruction, thrombotic thrombocytopenic purpura (TTP), extracorporal circulation such as renal dialysis, hemangioma, destruction by immune complex such as idiopathic thrombocytopenic purpura, Evans syndrome and drug allergy.

(3) Abnormal distribution of platelet, particularly retention of platelets and decreased production of platelets accompanied with splenoma and splenic hyperfunction, and bone marrow fibrosis accompanied by extramedullarly hematopoiesis.

(4) Diseases accompanying abnormal platelet functions such as abnormal platelet adhesion, abnormal platelet, and abnormal platelet coagulation, particularly thrombasthenia, afibrinogenemia, dysproteinemia such as myeloma, acute myelocytic leukemia, diabetes, myeloproliferative disorder, homocystinuria, storage pool disease, Bernard-Soulier syndrome, von Willebrand's disease.

BRIEF DESCRIPTION OF THE DRAWINGS

In the FIGS., * indicates $P<0.05$ and ** indicates $P<0.01$.

THE BEST MODE FOR CARRYING OUT THE PRESENT INVENTION

The present invention will be explained in more detail by the following examples.

Example 1

Purification of TCF-II

Purified TCF-II was obtained by cell culture according to the method disclosed in WO90/10651 or disclosed by Higashio, K. et al. (B.B.R.C., 170, 397–404, 1990).

Human fibroblast cells, IMR-90 (ATCC CCL 186), $3\times10^6$ cells, were inoculated in 100 ml of DMEM medium containing 5% calf serum in a roller bottle and cultured by rotating at a rate of 0.5–2/min. for seven days. The culture was continued up to total cell numbers of $1\times10^7$ cells in total, the proliferated cells were trypsinited and collected at the bottom of the bottle. In the bottle, 100 g of sterilized 5–9 mesh ceramic (Toshiba Ceramic Co., Ltd.) was placed and cultured for 24 hrs. upon standing. Then, 500 ml of the culture medium shown above was added to the bottle and cultured further. The total culture medium was recovered every 7–10 days and fresh culture medium was supplied for further culture. Thus, the culture was continued for two months and the culture broth of four l/bottle was recovered.

The combined culture solution showed specific activity of 32 U/ml.

Ultrafiltration of 750 l of the cultured solution was performed using a membrane filter (Amicon Corp., MW 6,000 cut) and TCF-II in the concentrate was purified by chromatographies consisting of five steps using CM Sephadex C-50 (Pharmacia Biosystems Corp.), ConA Sepharose (Pharmacia Biosystems Corp.), MonoS column (Pharmacia Biosystems Corp.) and heparin Sepharose (Pharmacia Biosystems Corp.). The purified TCF-II has specific activity of 5,248,000 U/mg.

Example 2

Production of recombinant TCF-II

TCF-II gene recombinant cells were cultured according to the method disclosed in WO92/01053 and purified TCF-II was obtained. Transformed Namalwa cells were cultured and 20 l of the culture solution was obtained. The culture solution was treated successively by chromatographies using CM-Sephadex C-50 column, Con-A Sepharose CL-6B column and MonoS column to give approximately 11 mg of active TCF-II.

Example 3

Production of pharmaceutical compositions of TCF-II

In the present examples, recombinant TCF-II obtained by Example 2 was used for the production of injection preparations.

(1) TCF-II 20 μg
Human serum albumin 100 mg

This composition was dissolved in 0.01M PBS at pH 7.0 and adjusted to 20 ml in total. The solution was sterilized, divided into vials (2 ml each), lyophilized and sealed.

| (2) TCF-II | 40 μg |
|---|---|
| Tween 80 | 1 mg |
| Human serum albumin | 100 mg |

This composition was dissolved in a saline solution for injection and adjusted to 20 ml in total. The solution was sterilized, divided into vials (2 ml each), lyophilized and sealed.

| (3) TCF-II | 20 μg |
|---|---|
| Tween 80 | 2 mg |
| Sorbitol | 4 g |

This composition was dissolved in 0.01M PBS at pH 7.0 and adjusted to 20 ml in total. The solution was sterilized, divided into vials (2 ml each), lyophilized and sealed.

| (4) TCF-II | 40 μg |
|---|---|
| Tween 80 | 2 mg |
| Glycine | 2 g |

This composition was dissolved in a saline solution for injection and adjusted to 20 ml in total. The solution was sterilized, divided into vials (2 ml each), lyophilized and sealed.

| (5) TCF-II | 40 μg |
|---|---|
| Tween 80 | 1 mg |
| Sorbitol | 2 g |
| Glycine | 1 g |

This composition was dissolved in a saline solution for injection and adjusted to 20 ml in total. The solution was sterilized, divided into vials (2 ml each), lyophilized and sealed.

| (6) TCF-II | 20 μg |
|---|---|
| Sorbitol | 4 g |
| Human serum albumin | 50 mg |

This composition was dissolved in 0.01M PBS at pH 7.0 and adjusted to 20 ml in total. The solution was sterilized, divided into vials (2 ml each), lyophilized and sealed.

| (7) TCF-II | 40 μg |
|---|---|
| Glycine | 2 g |
| Human serum albumin | 50 mg |

This composition was dissolved in a saline solution for injection and adjusted to 20 ml in total. The solution was sterilized, divided into vials (2 ml each), lyophilized and sealed.

(8) TCF- II 10 mg
Human serum albumin 100 mg

This composition was dissolved in 0.01M PBS at pH 7.0 and adjusted to 20 ml in total. The solution was sterilized, divided into vials (2 ml each), lyophilized and sealed.

Above mentioned TCF-II pharmaceutical preparations shown by (1) to (8) can be used for the treatment of abnormal blood coagulation and prevention of decrease of platelet count caused by administration of antitumor agents according to the above mentioned dosage.

Treatment agents to abnormal blood coagulation containing TCF-II as an effective ingredient are provided by the present invention. Hereinafter, test experiments with the treatment agents prepared according to the present invention will be shown to confirm the therapeutic effects and explain the present invention.

Experiment 1

Effects on the increase of platelet count and on prothrombin time (1) Method

Male Wistar rats, seven week old, six in one group, were used for the experiments. TCF-II was intravenously administered every 12 hrs., 28 times in total repeatedly at doses of 0 (zero), 5, 50, 500, and 5,000 μg/kg, respectively, and blood was drawn at 12 hrs. after the final administration to determine platelet count and prothrombin time.

The injection preparation of TCF-II was prepared by dissolving TCF-II in 10 mM phosphate buffer, pH 6.8–7.2, containing 0.01% Tween 80, 0.25% human serum albumin and 0.15M NaCl. The preparation was used in all the following experiments.

(2) Results

Figure 1:
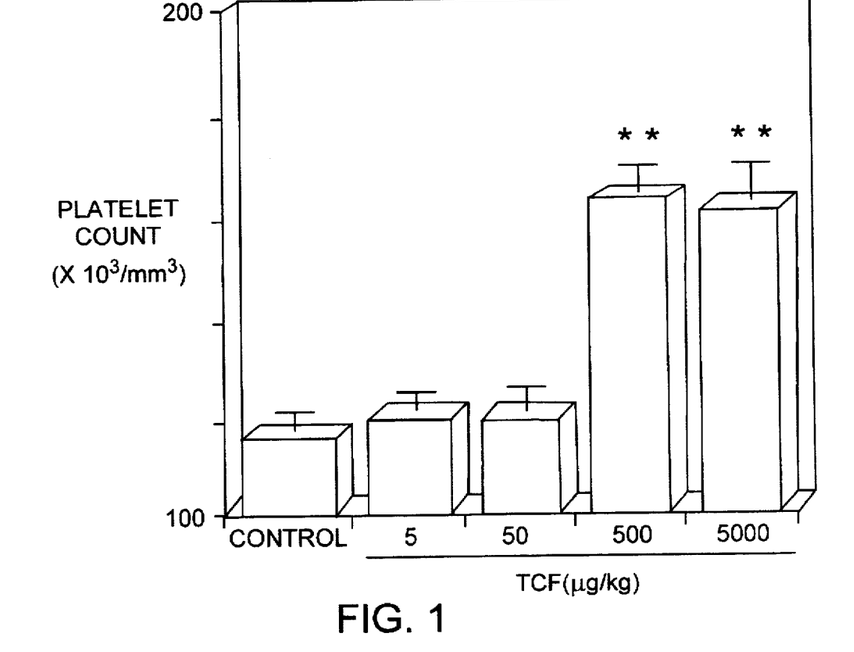
FIG. 1 shows the increase of platelet count by administration of the agent of the present invention in healthy rats.
Figure 2:
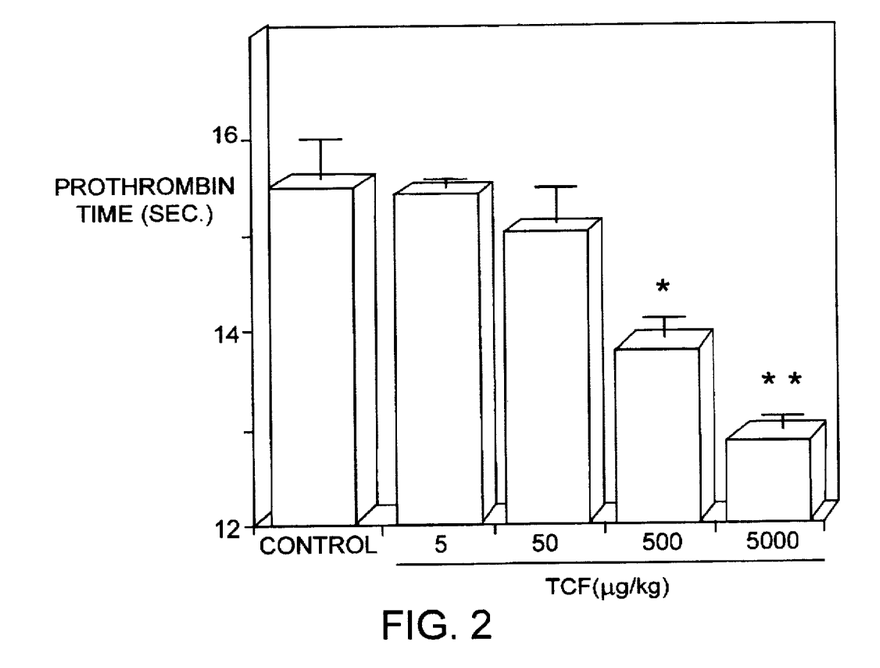
FIG. 2 shows the shortening effect of prothrombin time by administration of the agent of the present invention in healthy rats.

Increase of platelet count (FIG. 1) and shortening of prothrombin time (FIG. 2) were dose dependently observed. Both parameters showed marked improvement at doses of 500 µ/kg or over. The therapeutic effect on abnormal blood coagulation was confirmed.

Experiment 2

Effect on prothrombin time, plasma fibrinogen level and thrombotest value in blood coagulation disturbed rats by hepatectomy Coagulating factors are produced in the liver, thus rats with decreased coagulation ability were prepared by the hepatectomy and the effect of TCF-II was confirmed using these model animals.

(1) Method

In seven week old male Wistar rats, six in one group, 70% of the liver was resected and TCF-II was intravenously administered repeatedly to these rats at doses of 0 (zero), 20, 100 and 500 µg/kg, respectively, every 12 hrs. for two days, four times in total. The blood was drawn at 48 hrs. after the start of the administration and prothrombin time, plasma fibrinogen level and thrombotest value were determined.

(2) Results

Figure 3:
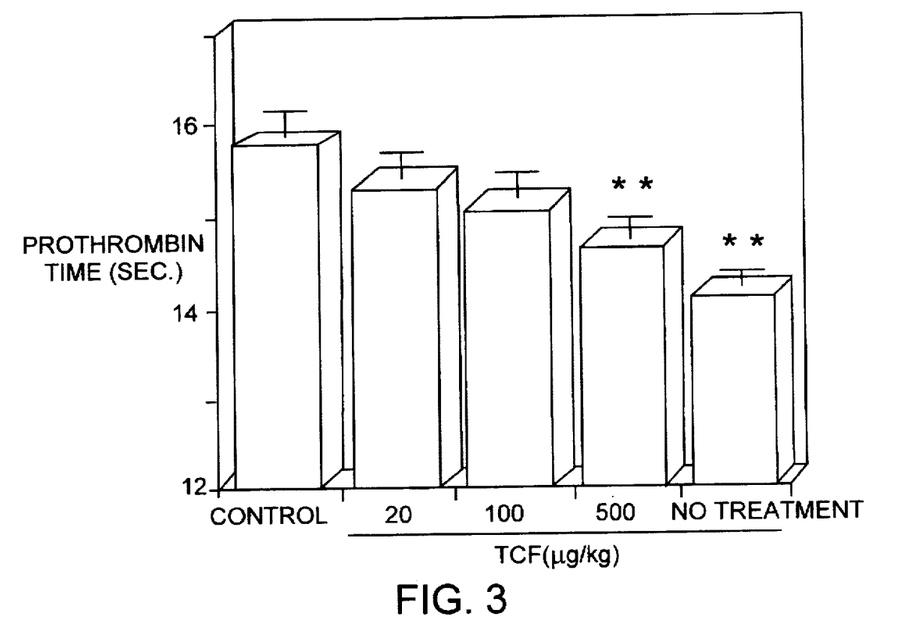
FIG. 3 shows the shortening effect of prothrombin time in blood coagulation disturbed rats by 70% hepatectomy followed by administration of the treatment agent of the present invention.
Figure 4:
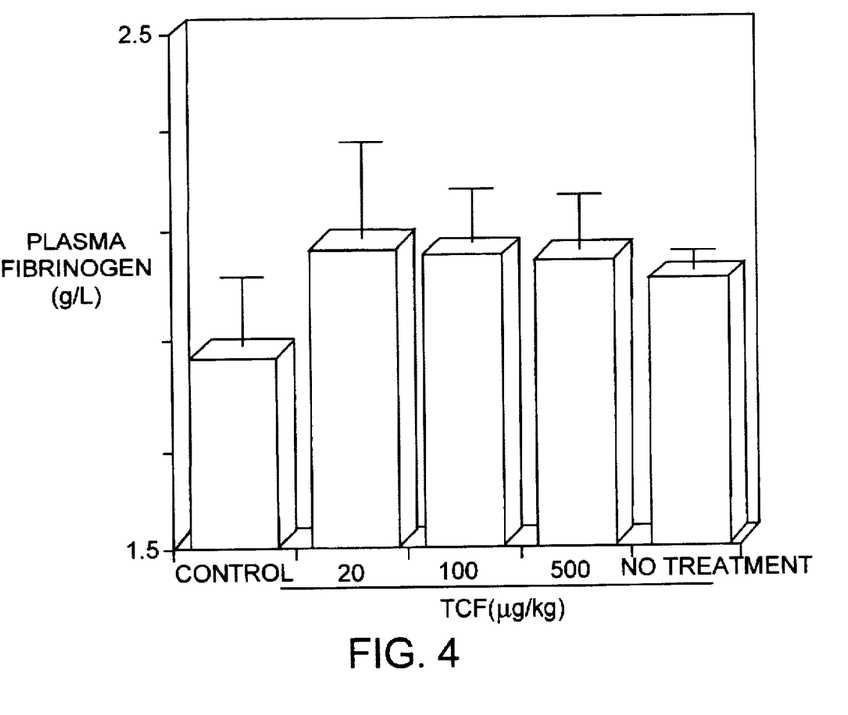
FIG. 4 shows the increase of plasma fibrinogen in blood coagulation disturbed rats by 70% hepatectomy followed by administration of the treatment agent of the present invention.
Figure 5:
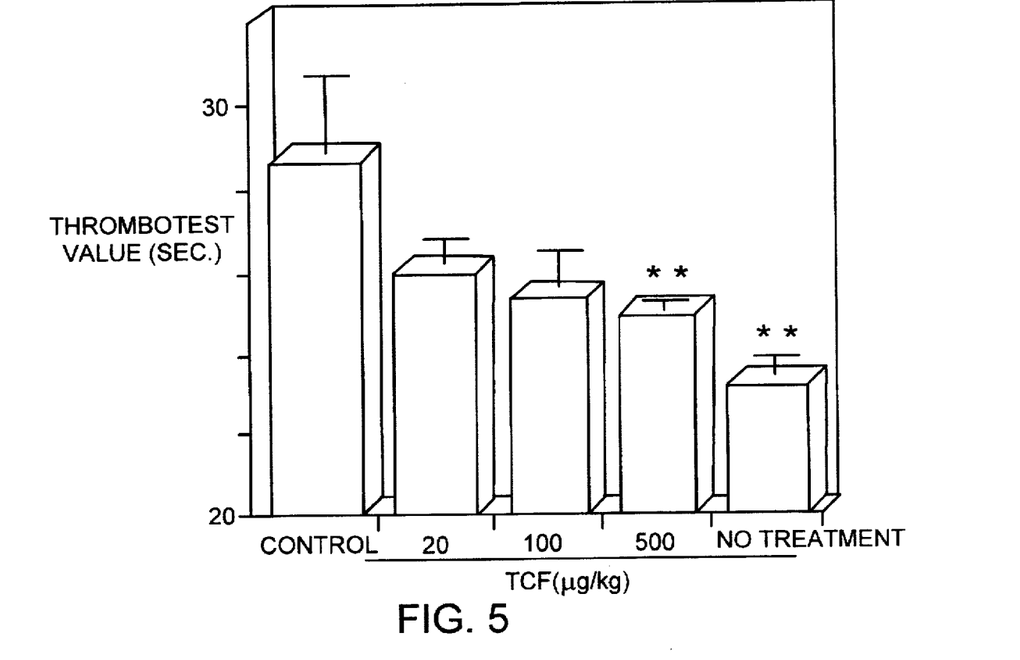
FIG. 5 shows the shortening of thrombotest value in blood coagulation disturbed rats by 70% hepatectomy followed by administration of the treatment agent of the present invention.

Shortening of prothrombin time (FIG. 3), increase of plasma fibrinogen (FIG. 4) and shortening of thrombotest value (FIG. 5) were observed with the administration of TCF-II. The therapeutic effect of the present invention on the liver oriented disease of blood coagulation is confirmed.

Experiment 3

Therapeutic effect of TCF-II administration rat model with decreased antithrombin III (1) Method To seven week old male Wistar rats, 10 in one group, 250 mg/kg/day of DL-ethionine was administered for four days to prepare antithrombin III activity decreased model. TCF-II was administered to the model at doses of 0 (zero), 50 and 500 µg/kg, respectively, every 12 hrs. intervals. Prothrombin time, antithrombin III activity and thrombotest value were determined at 48 hrs. after the start of the administration.

(2) Results

Figure 6:
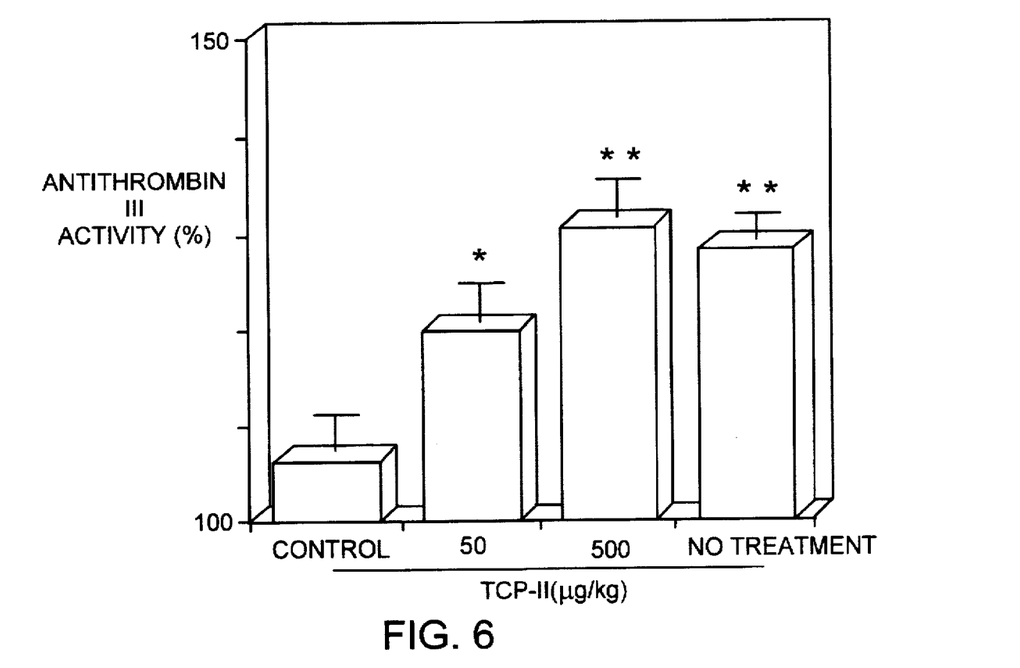
FIG. 6 shows the changes of antithrombin III activity in antithrombin III activity decreased rats by administration of the treatment agent of the present invention.
Figure 7:
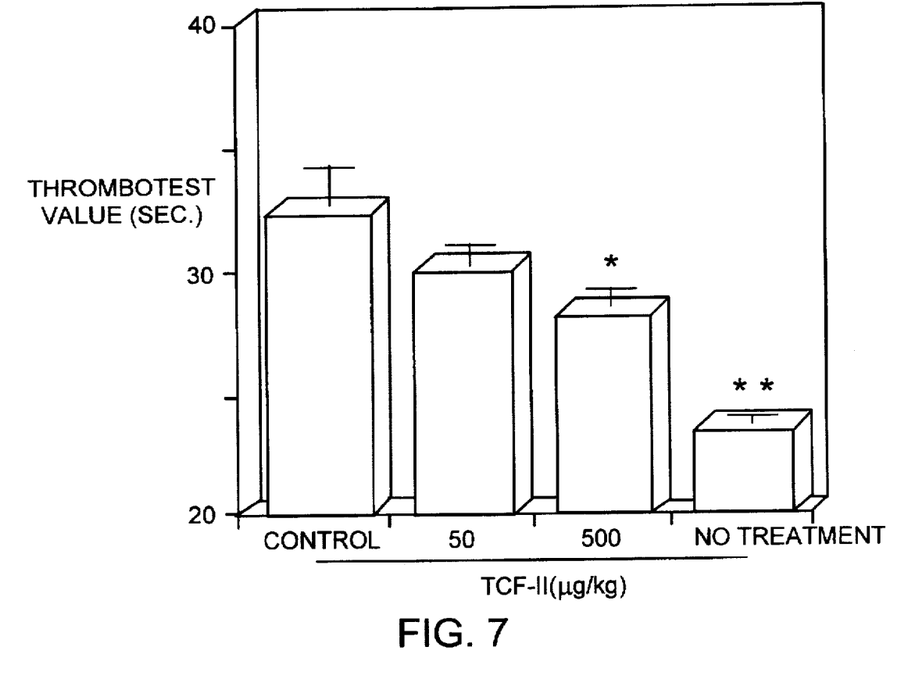
FIG. 7 shows the changes of thrombotest value in antithrombin III activity decreased rats by administration of the treatment agent of the present invention.
Figure 8:
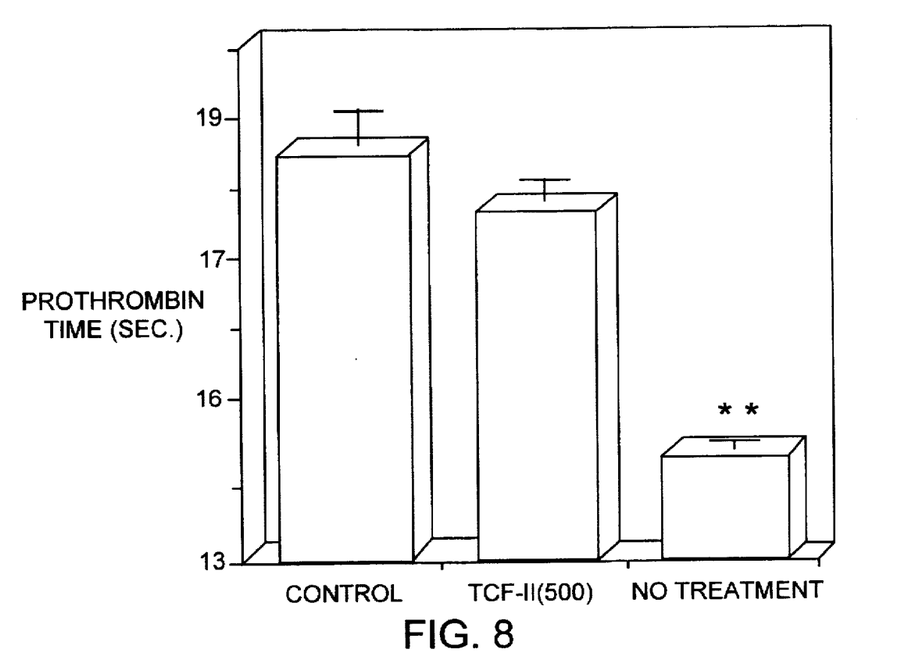
FIG. 8 shows the changes of prothrombin time in DIC rats by administration of the treatment agent of the present invention.

Recovery of antithrombin III activity (FIG. 6), shortenings of thrombotest value (FIG. 7) and prothrombin time (FIG. 8) were observed with the administration. The treatment agent of the present invention increased antithrombin III level confirming the efficacy for the treatment of blood coagulation disease.

Experiment 4

Therapeutic effect on DIC model (1) Method

To seven week old male Wistar rats, 10 in one group, 500 mg/kg of galactosamine was subcutaneously administered immediately after 70% hepatectomy to prepare a pathologic model of liver damage and DIC symptoms. TCF-II was intravenously administered repeatedly at a dose of 500 µg/kg every 12 hrs. for two days and four times in total. Blood was drawn at 48 hrs. after the start of the administration and prothrombin time, plasma fibrinogen level, antithrombin III level and thrombotest value were determined.

(2) Results

Figure 9:
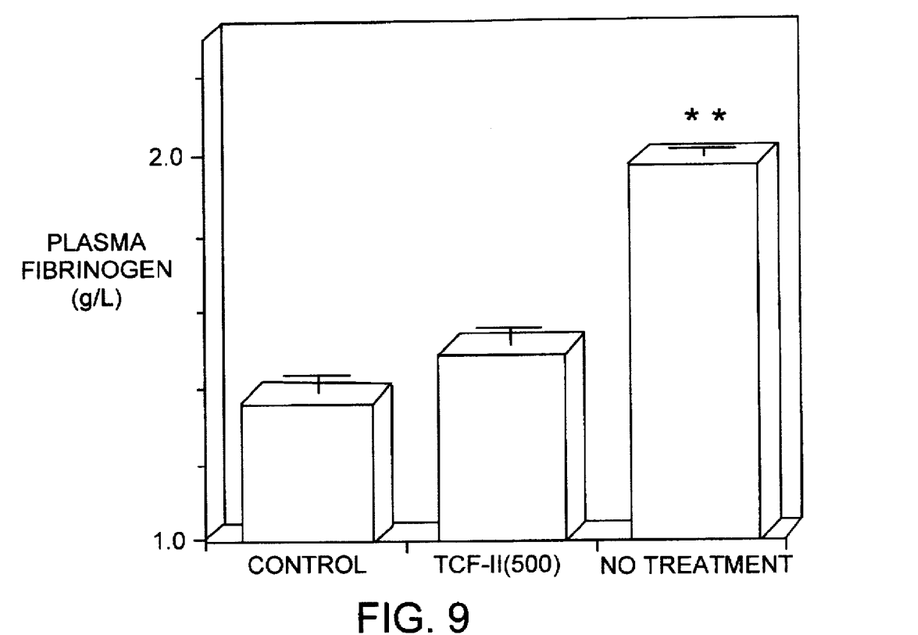
FIG. 9 shows the changes of plasma fibrinogen concentration in DIC rats by administration of the treatment agent of the present invention.
Figure 10:
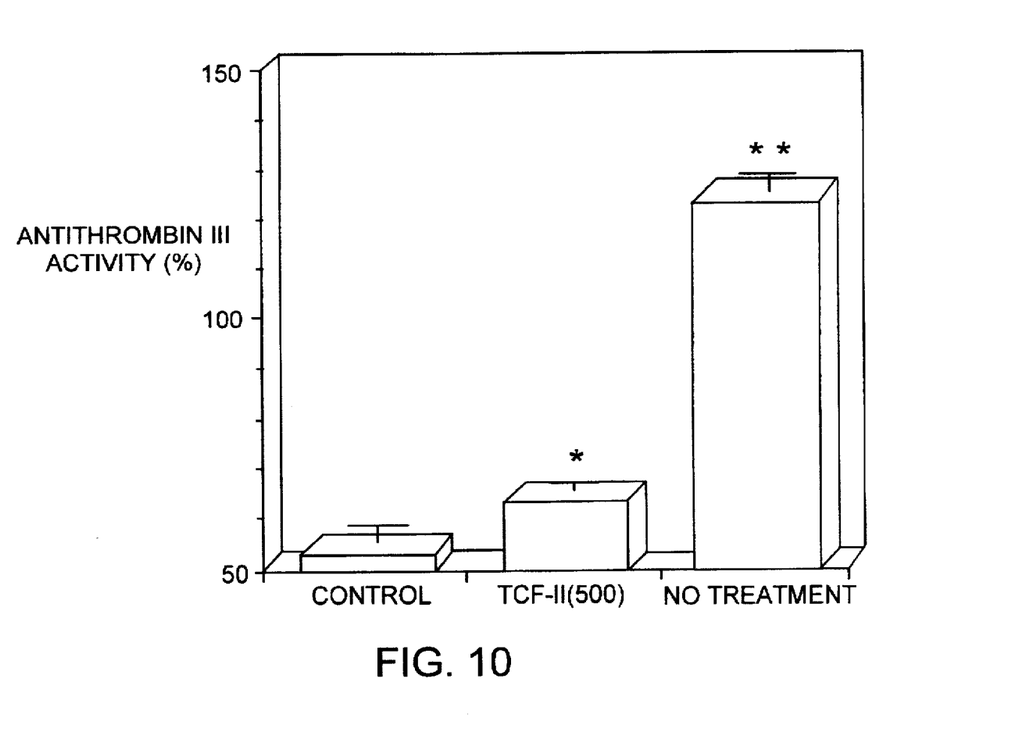
FIG. 10 shows the changes of antithrombin III activity in DIC rats by administration of the treatment agent of the present invention.
Figure 11:
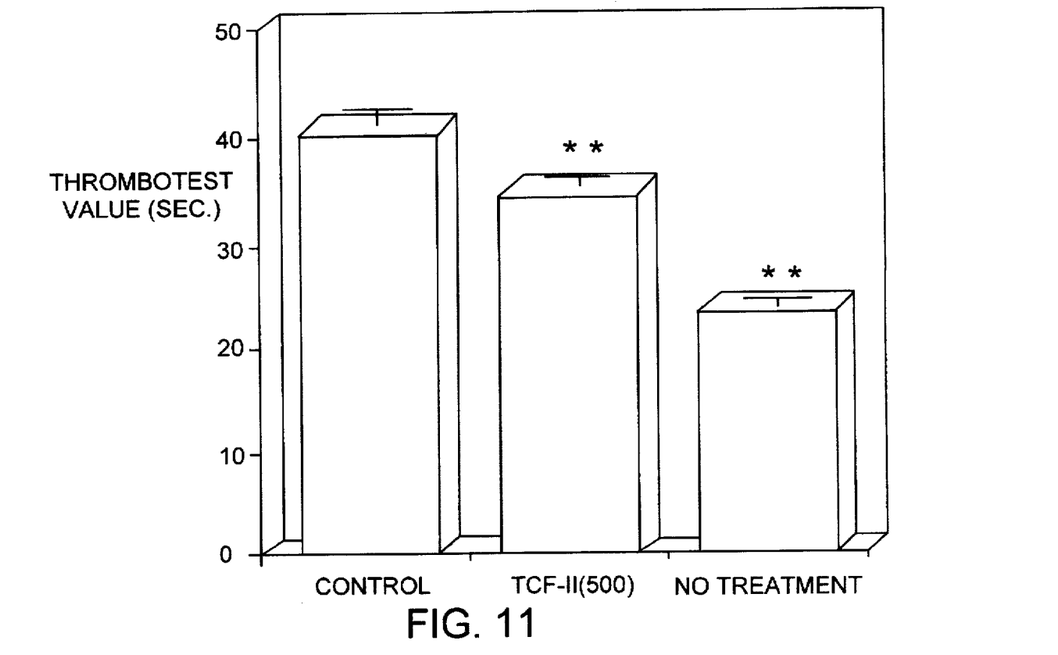
FIG. 11 shows the changes of thrombotest value in DIC rats by administration of the treatment agent of the present invention.
Figure 12:
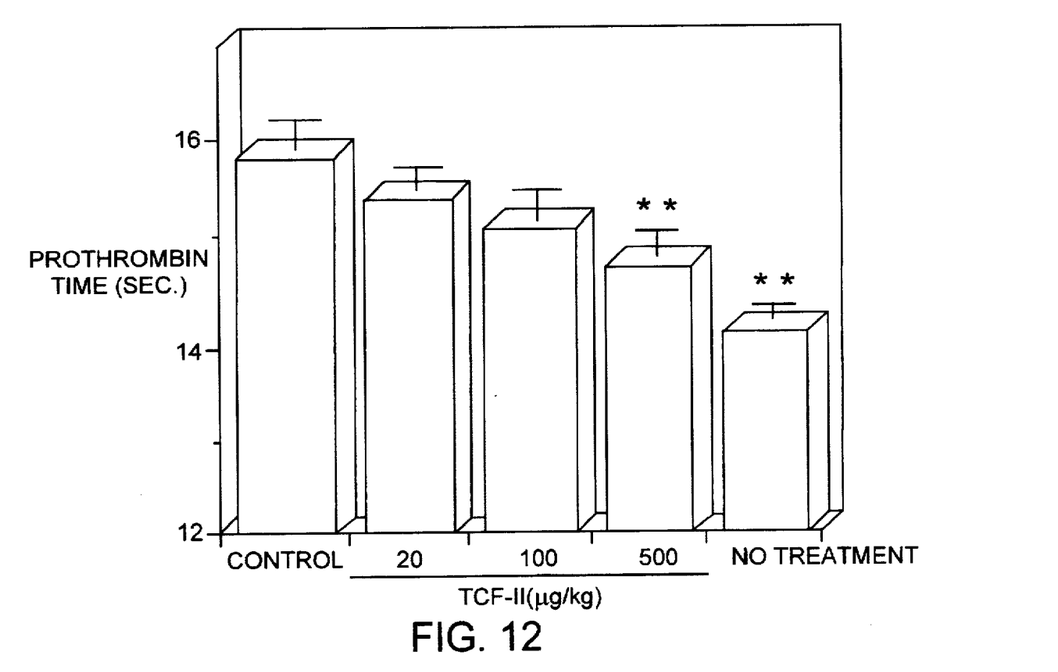
FIG. 12 shows the changes of prothrombin time in DIC rats by administration of the treatment agent of the present invention.

Increases of plasma fibrinogen level (FIG. 9) and antithrombin III activity (FIG. 10), and shortenings of thrombotest value (FIG. 11) and prothrombin time (FIG. 12) were observed with the administration. Thus, the efficacy of the present invention on disturbed blood coagulation due to DIC was confirmed.

As shown above, the therapeutic effect of the present invention to blood coagulation disease was confirmed.

Experiment 5

Therapeutic effect on platelet decreased model due to administration of antitumor agent (1) Method Seven week old male Wistar rats, 10 in one group, were administered once eight mg/kg of cisplatin (Shionogi & Co., Ltd.) to prepare platelet count decreased model.

Then, TCF-II was intravenously administered at a dose of one mg/kg immediately after the administration of cisplatin and at 12 hrs. intervals for seven days, repeatedly. The platelet count immediately before, days three and seven after the administration of cisplatin was determined with a multifunctional automatic blood counter (Sysmex E-7000). The results are shown in Table 1.

(2) Results

As shown in Table 1., a significant increase of platelet count was observed on and after day three of TCF-II administration. TCF-II maintained a significantly higher platelet count on day seven than that in control group of nine animals administered with the vehicle without TCF-II, which showed a marked decrease of platelet count.

Above results confirm the usefulness of TCF-II in the improvement of symptoms of various thrombocytopenia caused by the administration of antitumor agent.

TABLE 1

Changes of platelet count in cisplatin administered rat[a]

| | Cisplatin administered rat | | |
|---|---|---|---|
| | TCF-II | Control | Healthy rat |
| No. of animals | 10 | 9 | 10 |
| Before administration | 108.8 ± 3.4 | 100.7 ± 3.9 | 110.5 ± 2.8 |
| Day three after administration | 161.3 ± 5.2** | 137.9 ± 6.0 | 131.6 ± 5.2 |
| Day seven after administration | 32.8 ± 2.8** | 19.9 ± 2.8 | 140.4 ± 2.9** |

[a]:platelet count is expressed as mean ± S.D. and values with × 10³/mm³.
**:indicates significant difference at a level of p<0.01 from those in the control group.

Usefulness for Industry

The agent for the treatment of abnormal blood coagulation of the present invention can be used for the treatment of disseminated intravascular coagulation (DIC), and various symptoms accompanied with decreased platelet count.

We claim:

1. A method for treating a blood coagulation disorder comprising disseminated intravascular coagulation (DIC) or thrombocytopenia, comprising administering to a subject afflicted with the blood coagulation disorder a therapeutically effective amount of TCF-II.

2. The method of claim 1 wherein the blood coagulation disorder is accompanied by a decrease in platelet count resulting from decreased production of platelets, accelerated platelet destruction, abnormal distribution of platelets or abnormal platelet function.

3. The method of claim 1 wherein the mount of TCF-II administered comprises from about 500 to about 3,000 µg/kg/day.

4. The method of claim 1 wherein TCF-II is administered by injection.

5. The method of claim 1 wherein the TCF-II is in admixture with a pharmaceutically acceptable carrier.

6. The method of claim 1 wherein the TCF-II is recombinant.

7. A method for increasing platelet count in a subject afflicted with disseminated intravascular coagulation (DIC) or thrombocytopenia comprising administering to the subject an effective platelet-increasing amount of TCF-II.

8. The method of claim 7 wherein the mount of TCF-II administered comprises from about 500 to about 3,000 µg/kg/day.

9. The method of claim 7 wherein TCF-II is administered by injection.

10. The method of claim 7 wherein the TCF-II is in admixture with a pharmaceutically acceptable carrier.

11. The method of claim 7 wherein the TCF-II is recombinant.

* * * * *